United States Patent
Farrugia et al.

Patent Number: 5,542,430
Date of Patent: Aug. 6, 1996

[54] APPARATUS AND METHOD FOR DISCRIMINATING BETWEEN CARDIAC RHYTHMS ON THE BASIS OF THEIR MORPHOLOGY USING A NEURAL NETWORK

[75] Inventors: Steven Farrugia, Bexley; Hansen Yee, Wollstonecraft; Peter Nickolls, Vaucluse, all of Australia

[73] Assignee: Telectronics Pacing Systems, Inc., Englewood, Colo.

[21] Appl. No.: 306,993

[22] Filed: Sep. 16, 1994

[51] Int. Cl.$^6$ .................................................. A61B 5/046
[52] U.S. Cl. ........................................................ 128/705
[58] Field of Search ...................................... 128/702–705

[56]  References Cited

U.S. PATENT DOCUMENTS

| | | | |
|---|---|---|---|
| 3,554,187 | 1/1971 | Glassner et al. | 128/703 |
| 3,927,663 | 12/1975 | Russell et al. | 128/702 |
| 5,000,189 | 3/1991 | Throne et al. | 128/705 |
| 5,092,343 | 3/1992 | Spitzer et al. | 128/702 |
| 5,243,980 | 9/1993 | Mehra | 128/705 |
| 5,280,792 | 1/1994 | Leong et al. | 128/702 |

*Primary Examiner*—William E. Kamm
*Attorney, Agent, or Firm*—Gottlieb, Rackman & Reisman

[57]  ABSTRACT

An apparatus and a method are provided for coupling to a patient's heart for discriminating between tachycardias of physiological origin, and those of pathological origin having similar rates; and also for discriminating amongst those of pathological origin having similar rates. The apparatus includes transducers and/or sensing electrodes in either or both the atrium and/or ventricle. Also included are signal processing elements for determining the times of atrial and ventricular events and for extracting morphological features from the waveforms, and a neural network for classifying the heart rhythm. The method includes a step of discriminating between different types of heart rhythms having overlapping rates. The method utilizes atrial-atrial, ventricular-ventricular and atrio-ventricular intervals; integrated waveforms; sums of differences of waveform samples; rectified integrated bandpass filtered waveforms; numbers of zero crossings in the electrogram; area under the ventricular electrogram; and R wave slope, QR area and RS area of the electrogram.

6 Claims, 8 Drawing Sheets

APPARATUS AND METHOD FOR DISCRIMINATING BETWEEN CARDIAC RHYTHMS ON THE BASIS OF THEIR MORPHOLOGY USING A NEURAL NETWORK

FIELD OF THE INVENTION

This invention relates to implantable medical devices such as cardioverter/defibrillator/pacemakers which monitor cardiac rhythm using atrial and/or ventricular sensors. Such devices are each able to selectively provide one or more of the following therapies to a patient: defibrillation, cardioversion, bradycardia pacing or antitachycardia pacing. In particular, the invention relates to an apparatus and method that utilize a classification technique which discriminates among rhythms having overlapping ventricular rates. A patient is said to have overlapping ventricular rates when, at different times, the rate of one rhythm may be close to the rate of another rhythm by a relatively small difference of, say, less than 10 beats per minute. Such rhythms may be either physiological (e.g., normal sinus rhythm (NSR)) or pathological (e.g., slow ventricular tachycardia (SLVT or may stem from a supra-ventricular tachycardia (SVT)), and, therefore, require discrimination for the purpose of therapy.

Similarly, fast ventricular tachycardia (FVT), which can be treated by antitachycardia pacing, and slow ventricular fibrillation (SLVF), which must be treated by defibrillation shock, have overlapping heart rates.

The device and method described herein perform this discriminatory function.

BACKGROUND OF THE INVENTION

Some current medical devices designed to provide antitachycardia therapy and defibrillation therapy have attempted to discriminate between physiological (e.g., NSR) and pathological cardiac rhythms (e.g., SLVT) using the heart rate sensed by a single ventricular sensor. U.S. Pat. No. 4,875,483 to W. Vollmann et al, entitled "Implantable Cardiac Pacer with Programmable Antitachycardia Mechanisms", which issued on Oct. 24, 1989, discloses such a device. Others have attempted to discriminate between pathological cardiac rhythms requiring different therapies (e.g., FVT and SLVF), but having overlapping ventricular rates.

However, classification techniques which are based solely on ventricular rate parameters are unable to distinguish between physiological and pathological rhythms, or between different pathological rhythms that have overlapping ventricular rates. An important instance of this is NSR, which is a physiological rhythm, and SLVT, which is a pathological rhythm. A second important instance of this is FVT, which is a pathological rhythm which may be treated by antitachycardia pacing, and a SLVF, which is a pathological rhythm which must be treated by high voltage defibrillation shock.

The use of a neural network to match templates of different known rhythms with an unknown rhythm may overcome this particular problem. This is proposed in U.S. Pat. No. 5,092,343 to R. Spitzer et al, entitled "Waveform Analysis Apparatus and Method Using Neural Network Techniques", which issued on Mar. 3, 1992. The Spitzer et al. patent device offers only a partial solution to the above problem as it has an unacceptably long delay before reaching a decision and also an unacceptably high error rate. The reason for the long delay is that the device accumulates data to form a frequency histogram of signal amplitudes before beginning the next stage of the classification process. The device then divides the waveforms into different groups by means of frequency histograms each containing waveforms of similar amplitudes. The effect of this is to erroneously separate cardiac rhythms of the same type into different groups due to the variation in signal amplitude caused by respiration. Furthermore, the above device uses as the input, to a neural network contained therein, samples from the input waveforms, i.e. filtered signals with no features extracted. This is insufficient in terms of achieving a satisfactory classification accuracy.

Further prior art includes that described in an article written by Susan Lee entitled "Using a Translation—Invariant Neural Network to Diagnose Heart Arrhythmia", IEEE Engineering in Medicine and Biology 11th Annual Conference, Seattle, Wash., 1989. In this article, ventricular intracardiac electrograms (ICEG) underwent a translation invariance pre-processing by means of weighted sums of differences of signal samples before being passed to the input of the neural network. The theoretical advantage of this is that it is not necessary to accurately align each waveform with the neural network inputs. The disadvantage is that there is a loss of sensitivity and specificity and greatly increased processing time due to the multiplications required to calculate the weighted sums of differences.

An improved approach is described in the present invention in which signal peaks are used for alignment and the effect of jitter is removed by means of a simplified sums of differences procedure which does not require multiplications.

U.S. Pat. No. 5,251,626 issued Oct. 12, 1993 to P. Nickolls et al. for "Apparatus and Method for the Detection and Treatment of Arrhythmias Using a Neural Network" describes a system which includes a neural network having at least three hierarchical levels. A first lower level is used for classifying individual waveforms. A second higher level is used for diagnosing detected arrhythmias, and a third higher level operates for therapy application to a diagnosed arrhythmia. The present invention eliminates the need for a neural network at the first lower level and thereby provides a faster real time diagnosis of arrhythmias. Accordingly, the main object of this invention is to provide an improved apparatus and a method for discriminating among heart rhythms having overlapping ventricular rates on the basis of their morphology. The apparatus reliably discriminates between NSR and pathological rhythms, such as SLVTs and SVTs, and also reliably discriminates between other different pathological rhythms, such as FVT and SLVF, without undue delay and in such a way that the invention is suitable for use in an implantable cardioverter/defibrillator/pacemaker. Furthermore, real time classification is achieved with the present invention by aligning the extracted waveforms with the peaks of the signals from which they are extracted.

It is a further object of the invention to provide a classification technique which uses morphological features extracted from an electrogram as the input to a neural network.

It is a further object of the invention to provide a classification technique which continuously processes and classifies data.

SUMMARY OF THE INVENTION

Briefly stated, and in accordance with one embodiment of the invention, there are provided an apparatus and a method for discriminating between tachycardias of physiological origin, and those of pathological origin, having similar rates; and also for discriminating between different types of tachycardias of pathological origin, having similar rates. The apparatus includes at least one sensing electrode for registering the electrogram from the ventricle of the heart, and a signal processing element for extracting features from the electrogram.

Preferably, the apparatus includes two sensing electrodes for registering the respective electrograms from the atrium and the ventricle of the heart.

In an alternative arrangement, the apparatus includes transducers for registering the pressure of the blood flow in a selected chamber of the heart.

In another alternative arrangement, the apparatus includes transducers for registering the movement of a wall of a selected chamber of the heart.

The apparatus preferably includes a neural network which has as its input samples of the original electrogram and the features extracted from the electrogram.

The invention provides an apparatus and a method of discriminating between different types of heart rhythms having overlapping ventricular rates. The method utilizes morphological features extracted from the electrograms as a basis for classification by a neural network, in discriminating between heart rhythms.

The invention further provides an apparatus and a method of discriminating between heart rhythms having similar atrial and ventricular rates.

There is further provided an apparatus and a method for discriminating between tachycardias of physiological origin, and those of pathological origin having similar rates; and also for discriminating amongst those of pathological origin having similar rates. The apparatus includes transducers and/or sensing electrodes in either or both the atrium and the ventricle of the heart, signal processing elements for determining the times of atrial and ventricular events and for extracting morphological features from the waveforms, and a neural network for receiving the extracted features and for classifying the heart rhythms based on such features. The method includes a means for discriminating between different types of heart rhythms having overlapping rates. The method utilizes extraction of combinations of the following features for feeding to a neural network:

(i) atrial-atrial, ventricular-ventricular and atrio-ventricular intervals;

(ii) integrated waveforms;

(iii) sums of differences of waveform samples;

(iv) rectified integrated bandpass filtered waveform;

(v) numbers of zero crossings in the electrogram;

(vi) area under the ventricular electrogram; and (vii) R-wave slope, QR area and RS area of the electrogram.

BRIEF DESCRIPTION OF THE DRAWINGS

Further objects, features and advantages of this invention will become apparent upon consideration of the following detailed description thereof, taken in conjunction with the accompanying drawings, in which.

DETAILED DESCRIPTION OF THE INVENTION

Figure 1:
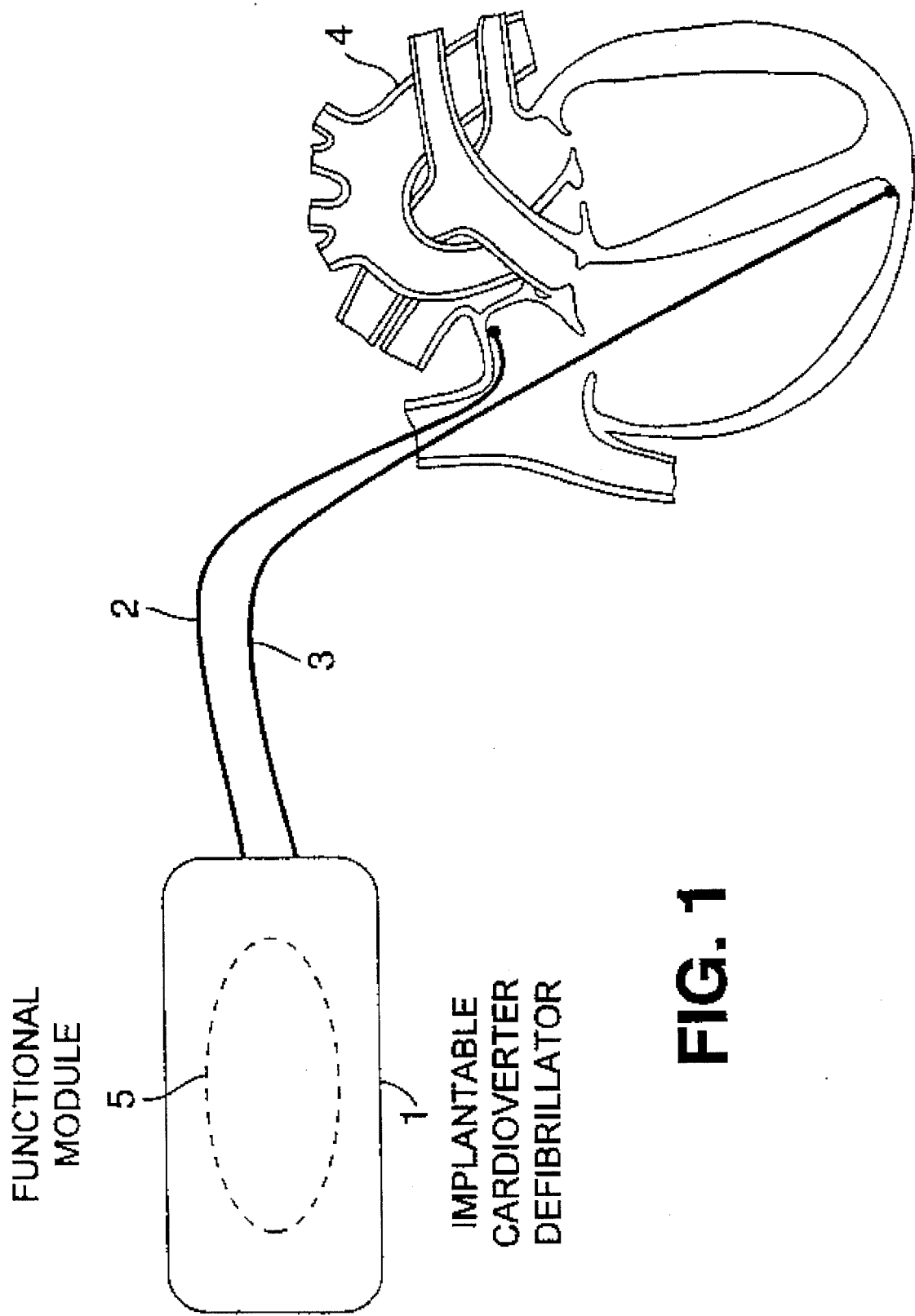
FIG. 1 depicts a schematic diagram of an implantable cardioverter/defibrillator (ICD) device employing atrial and ventricular sensing leads and including a functional module for heart rhythm classification.

Referring to FIG. 1, there is depicted a block diagram of an implantable cardioverter/defibrillator (ICD) device 1 having atrial and ventricular leads 2 and 3 respectively, connected to a patient's heart 4 for the sensing of atrial and ventricular events. In some formulations, the atrial lead may be omitted. Within the implantable cardiac device 1 is a functional module 5 containing ICD processing and control circuits, and containing a neural network for the classification of sensed heart rhythms using morphological features derived from the sensed electrical signals and/or from other pressure flow or movement signals initiated by the ventricles and atria.

As indicated above, the different types of heart rhythms on which the invention is focused have overlapping ventricular rates. The method employed in the present invention for discriminating between the different rhythms focuses on the differences in the shape and size of the waveforms.

Figure 2:
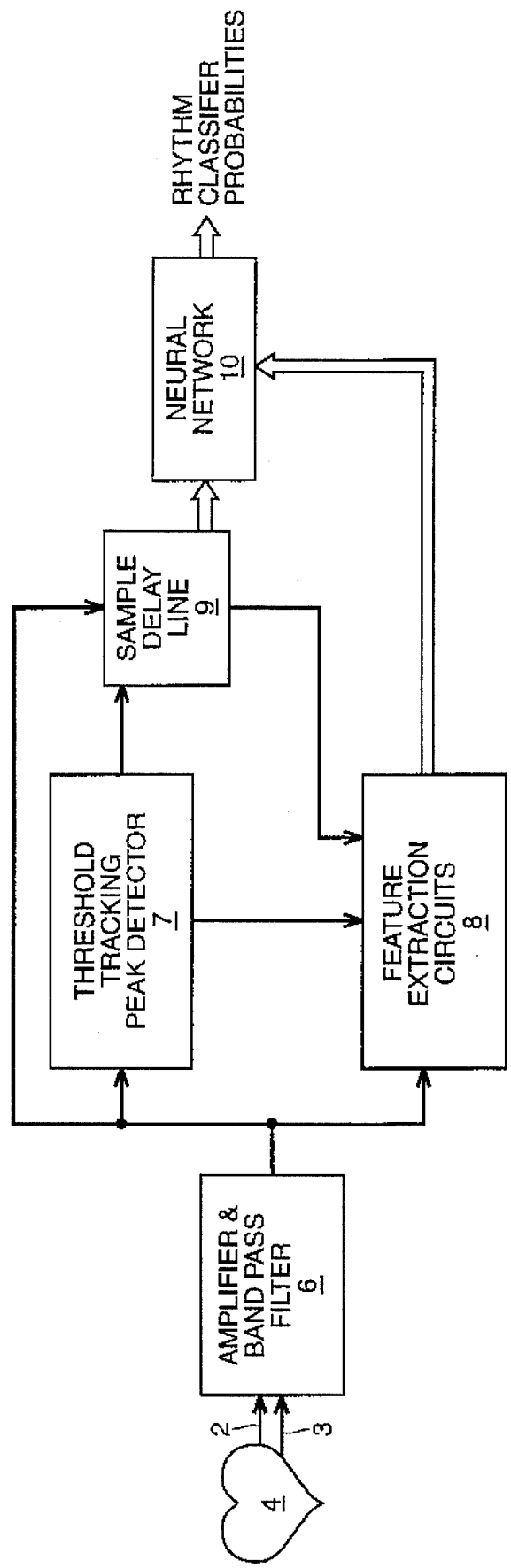
FIG. 2 shows a block diagram of the pre-processing and feature extraction circuits and the neural network that produces the heart rhythm classification.

Referring now to FIG. 2, the method for discriminating between these different types of heart rhythms is disclosed. Alternative methods may use only some of these elements, and the ordering of the elements employed in FIG. 2 is not necessarily restricted to that shown in the Figure.

The electrocardiographic signal from the heart 4 passes via the leads 2, 3 to an amplifier 6 which incorporates a band pass filter. The leads may be connected to sensor electrodes or pressure transducers, not shown, as described, for example, in U.S. Pat. No. 5,156,157 entitled "Catheter-mounted Dappler Ultrasound Transducer and Signal Processor", which issued Oct. 20, 1992 to Valenta, Jr. et al. and is assigned to the assignee of the present invention. A typical implementation of the band pass filter has a lower 3 dB cut-off frequency of 0.2 Hz and an upper 3 dB cutoff frequency of 70 Hz. Other variations of the pass band of this filter are possible.

The output signal of the amplifier and band pass filter 6 passes to a threshold tracking peak detector circuit 7 which is more fully described in U.S. patent application Ser. No. 07/901,644 by J. Wickham, filed Jun. 22, 1992, entitled "Intra-cardiac Electrogram Sensing In An Arrhythmia Control System", which is assigned to the assignee of the present invention, and is hereby incorporated by reference. The threshold tracking peak detector is used to provide a reference time for sampling the electrocardiogram to provide direct input to a neural network 10 via a sample delay line 9, and also to allow features to be extracted from the electrocardiogram at appropriate times. Feature extraction circuits 8 extract morphological features relating to the amplitude and shape of the electrocardiogram and pass these to the inputs of the neural network.

The sample delay line 9 continuously passes successive samples of the electrocardiogram or other signals through it. A timing signal from the threshold tracking peak detector 7 allows samples symmetrically placed about a waveform peak to be input to the neural network 10. A typical implementation of the sample delay line allows ten samples from each waveform to be input simultaneously to the neural network. Useful numbers range from 3 to 100 samples.

The feature extraction circuits 8 are used to provide the following signals: integrated waveform, interval between complexes, sums of differences between samples, rectified integrated bandpass filtered waveform, number of zero crossings in a ventricular depolarization, area under the ventricular depolarization complex, R-wave gradient, QR area, and RS area. In addition, true averages or moving averages of these features may also be used as inputs to the neural network 10. The extraction of these features will now be discussed in further detail.

FEATURE EXTRACTION GENERALLY

The features to be extracted may be extracted from the unfiltered or filtered signal by analog or digital processing, or by a combination of the two. The signal may be any single one or combination of the following: an electrogram from the endocardial or epicardial surfaces of any part of the four chambers of the heart (left or right ventricle, left or right atrium); a pressure waveform from any of the four chambers of the heart; an impedance signal at any frequency measured from any chamber or between a chamber and a reference electrode outside the heart; a flow signal from an ultrasonic transducer in the heart; a heart wall movement signal from an ultrasonic transducer.

Figure 3:
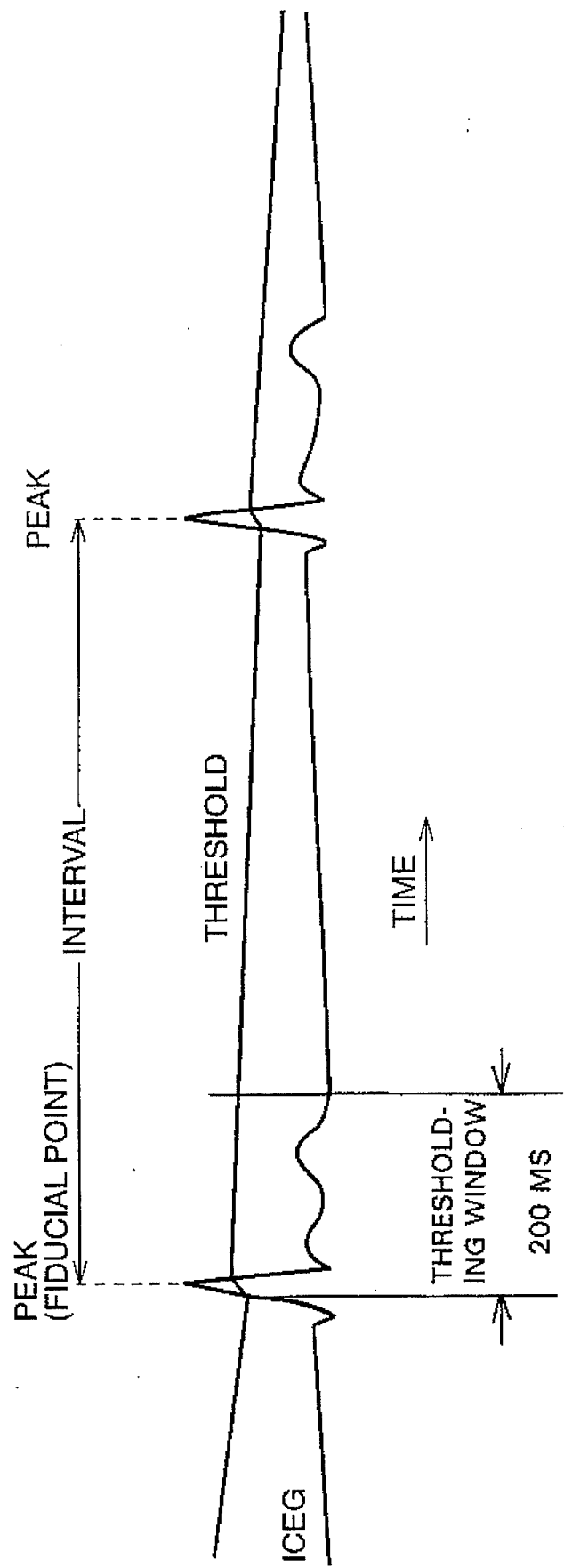
FIG. 3 shows a typical input signal, in this instance a ventricular intracardiac electrogram (ICEG), although other input signals may also be use, in relation to a peak detector threshold that is used to determine intervals between QRS complexes.

For many of the features, the threshold tracking peak detector circuit 7 is used to find a fiducial point in the waveform. This point is the maximum positive or minimum negative peak within a window of about 200 ms commencing from the point at which the threshold is being exceeded by the ICEG waveform, as shown in FIG. 3. This window is referred to as the threshold window and is selected so that it is wide enough to handle different rhythms and waveforms.

INTEGRATED WAVEFORM FEATURE

The waveform is integrated symmetrically about its peak fiducial point for a period which may range from 20 ms to 1000 ms on either side of this point. In a typical implementation, integration is performed for a period of 150 ms on each side of the fiducial point.

Figure 4:
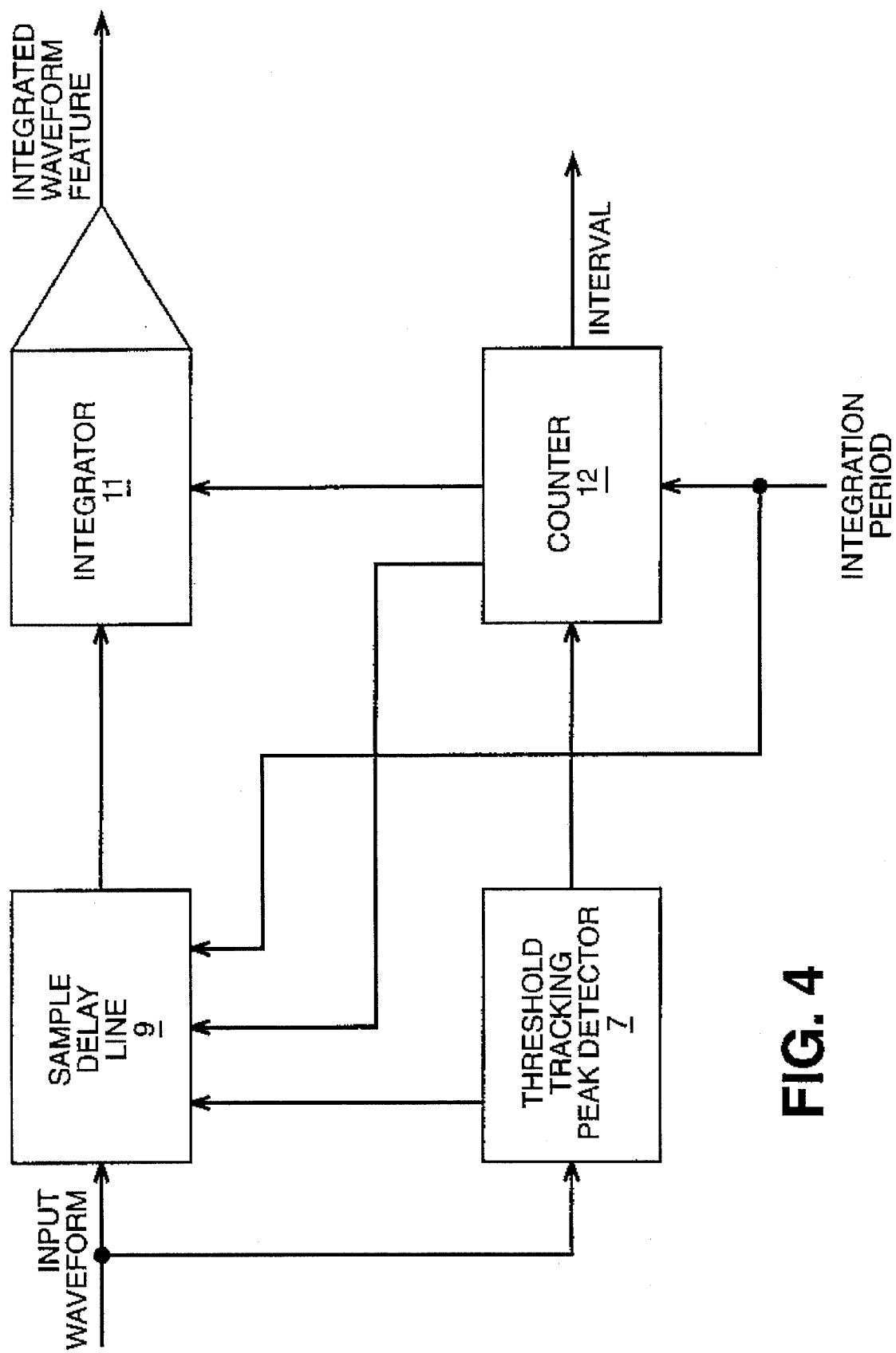
FIG. 4 is a block diagram of the circuitry required for extracting the integrated waveform and interval between complexes features from the input waveforms.

Referring to FIGS. 1 and 4, the sampled waveform, which may be derived from either an atrial or a ventricular signal or separately from both, and which is stored in the delay line 9, is integrated by digital summation or by an analog integrator 11 for the required period. A predetermined integration period is used to set a counter 12 and to tap the signal from the appropriate point of the delay line. The counter controls the beginning and end of the integration period. Integration is by direct summation of the digitized signal or by accumulation of charge in a capacitor forming part of the feed-back circuit of an operational amplifier (not shown).

The output of the integrator 11 is the required integrated waveform feature. It may be directly input to the neural network 10, or may undergo further processing before the neural network. The further processing may be by taking a fixed or moving average of the output of the integrator. For a fixed average the previous one to 50 beats (one to 50 waveform peaks detected) or the previous 200 ms to ten sec is averaged. In a typical application the previous eight beats or the previous four sec is averaged. For a moving average the scaling factor for the most recent beat ranges from 0.01 to 0.8. In a typical application, a figure of 0.125 is used, with the total input to the mean calculation being normalized to 1.0.

INTERVAL BETWEEN COMPLEXES FEATURE

Referring to FIGS. 2, 3 and 4, the interval between complexes is generated by the counter 12, using the fiducial markers produced by the threshold tracking peak detection circuit 7.

The interval signal may be input to the neural network 10, or may be further processed by taking a fixed or moving average in the same manner as for the Integrated Waveform feature.

The intervals may be measured between successive ventricular complexes, between successive atrial complexes or between successive atrial and ventricular complexes or any combination of some or all of these measurements.

By this means, it is possible for the neural network 10 to discriminate (i) between rhythms having different rates, such as bradycardia, resting sinus rhythm and the tachycardias, or (ii) between rhythms having similar rates but different sequencing between atrial and ventricular events, such as sinus tachycardia, ventricular tachycardia, atrial fibrillation and other supraventricular tachycardias.

SUMS OF DIFFERENCES BETWEEN SAMPLES FEATURE

Samples of the waveform are taken at 40 ms intervals symmetrically about the peak of each waveform. Sums of differences are formed as follows:

$$\sum_{i=1}^{N-k} ABS(X_i - X_{i+k}) \qquad (1)$$

where $X_i$ is the amplitude of the waveform at the i'th sample, and k may range from one to N/2.

N may be in the range five to 200. In the typical practice N is chosen as 40. It is not necessary to choose all values of k. In typical practice k has the values 1, 4, 8, 12, 16 so that five sums of differences are chosen. This method has the advantage of not requiring any multiplication and is easily implemented in digital form or using summing operational amplifiers in analog form. It is also possible to sample the waveform at 80, 20, 10 and 5 ms intervals.

The outputs of any or all of these summations may be fed directly into the neural network 10, or may be further processed by a fixed or moving average filter as described previously.

RECTIFIED INTEGRATED BANDPASS FILTERED WAVEFORM FEATURE

Figure 5:
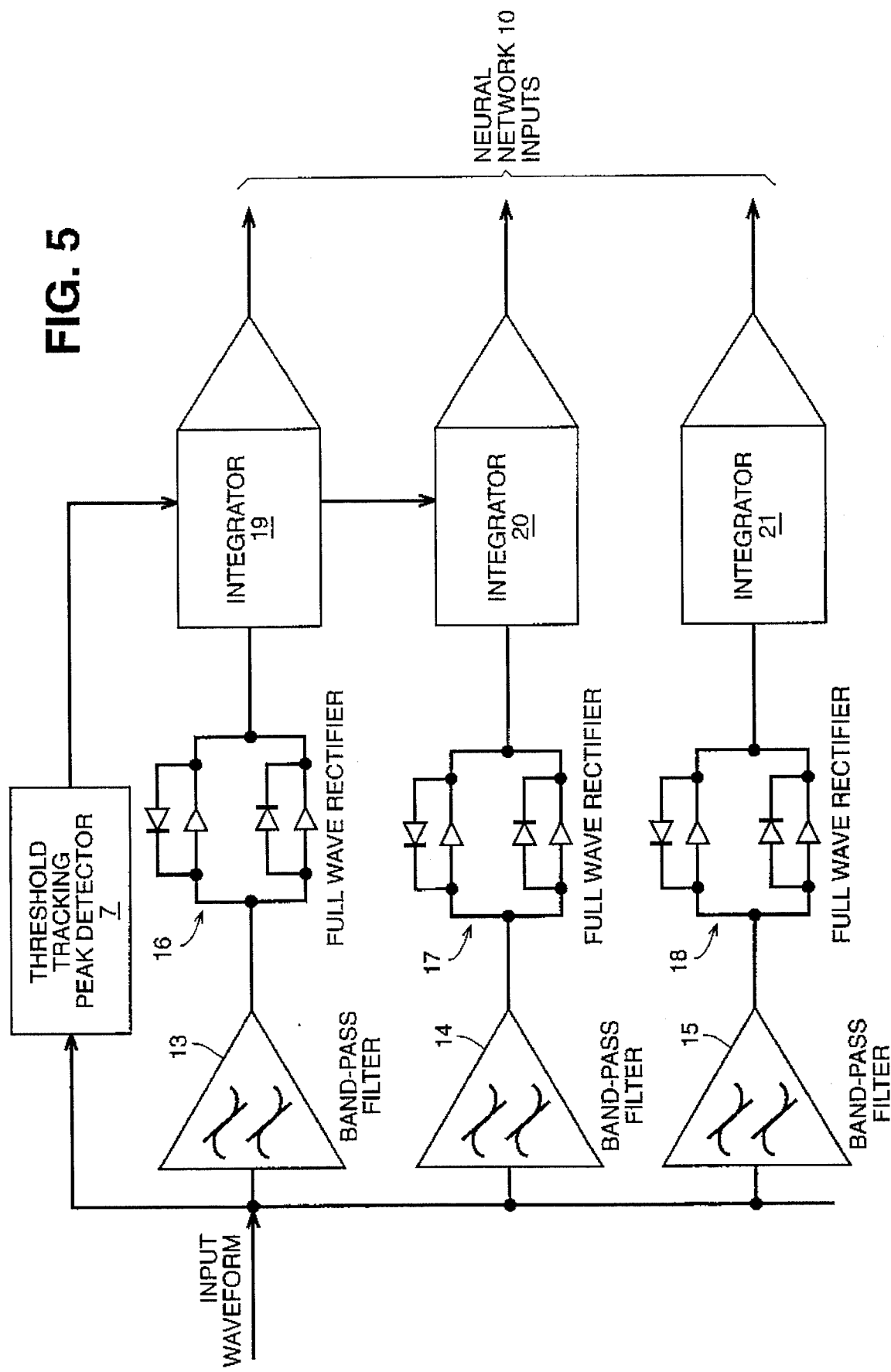
FIG. 5 visa block diagram of the circuitry required for extracting rectified integrated bandpass filtered features from the input waveforms.

The waveform is input in parallel to three or more filters. These filters may be implemented by Fourier transformation to the frequency domain, filtering and reverse transformation while using an appropriate window such as the Hanning window. Alternatively, a digital or analog filter in the time domain of second order or higher may be used. The center frequencies of these filters are set in the range five to 100 Hz. The bandwidth of the filters is in the range of three to 40 Hz. Referring to FIG. 5, in a typical implementation, three second order analog filters 13, 14 and 15 are used with center frequencies of 12, 26 and 40 Hz, each with a bandwidth of 6 Hz.

The output of each filter is then rectified by respective rectifiers 16, 17, and 18, and integrated by respective integrators 19, 20 and 21, over a time period of up to one sec. Further fixed or moving average processing may also be done. Typically, the integration period is one interval between heart beats so that the integrator is reset by the peak detector circuit 7.

NUMBER OF ZERO CROSSINGS IN A VENTRICULAR DEPOLARIZATION FEATURE

Figure 6:
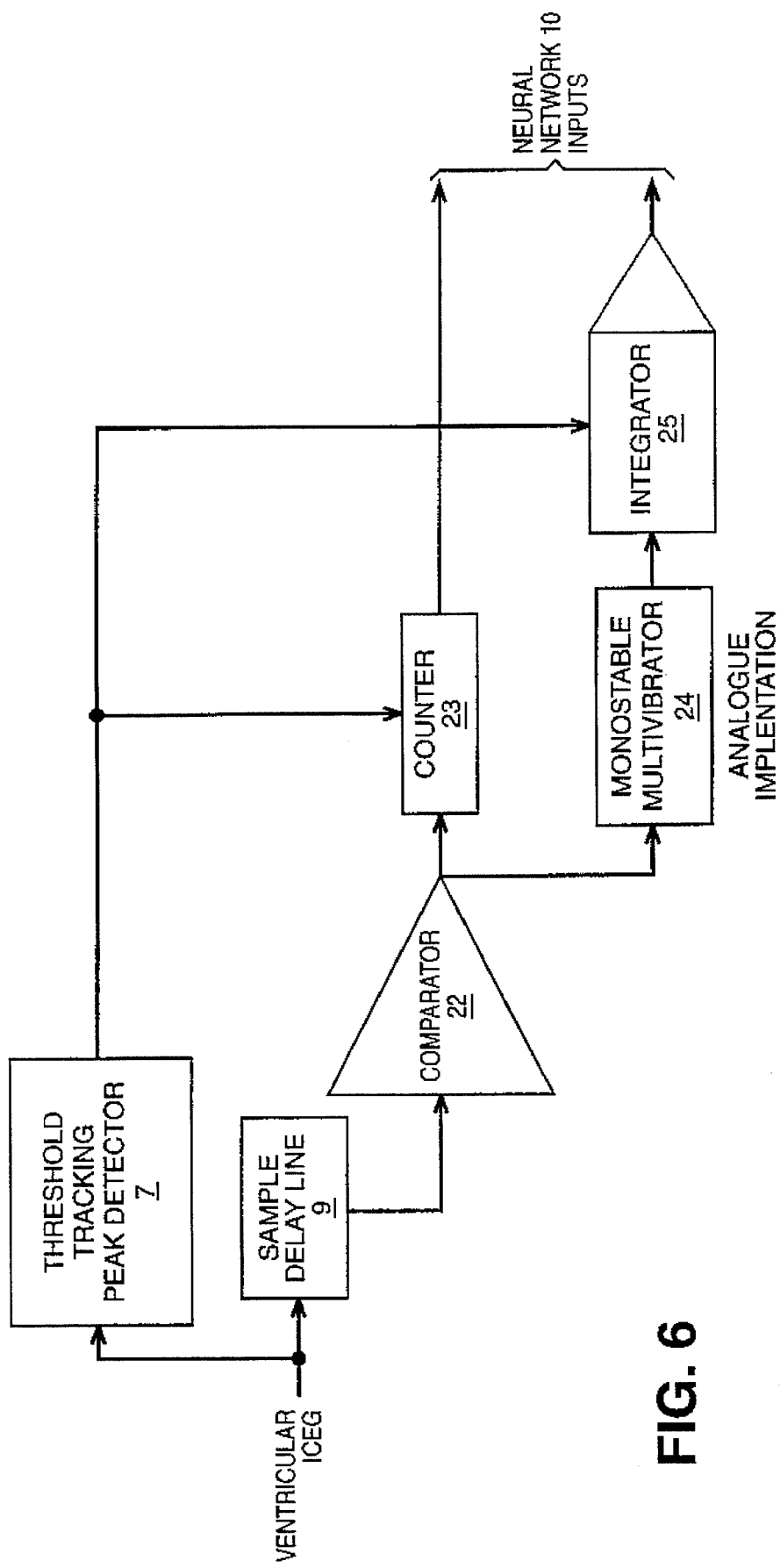
FIG. 6 is a block diagram showing two alternative ways of extracting the number of zero crossings feature from the ventricular ICBG.

Referring to FIG. 6, the ICEG from the ventricular lead 3 (FIG. 1) is tapped from sample delay line 9 under the control of the threshold tracking peak detector circuit 7, so that the signal about each ventricular complex is taken. It is passed through a comparator 22 with enough hysteresis to ensure it is not affected by noise. The output of the comparator may go to a counter 23 in a digital implementation, or to an edge triggered monostable multivibrator 24 whose output is integrated by an integrator 25 in an analog implementation. The subsequent outputs pass to the input of the neural network 10, with or without further processing by averaging as described previously. In a typical implementation the hysteresis of the comparator is set to ±150 uV and the counter or integration time is set to one sec or is re-set by the threshold tracking peak detector.

R WAVE GRADIENT FEATURE

Figure 7:
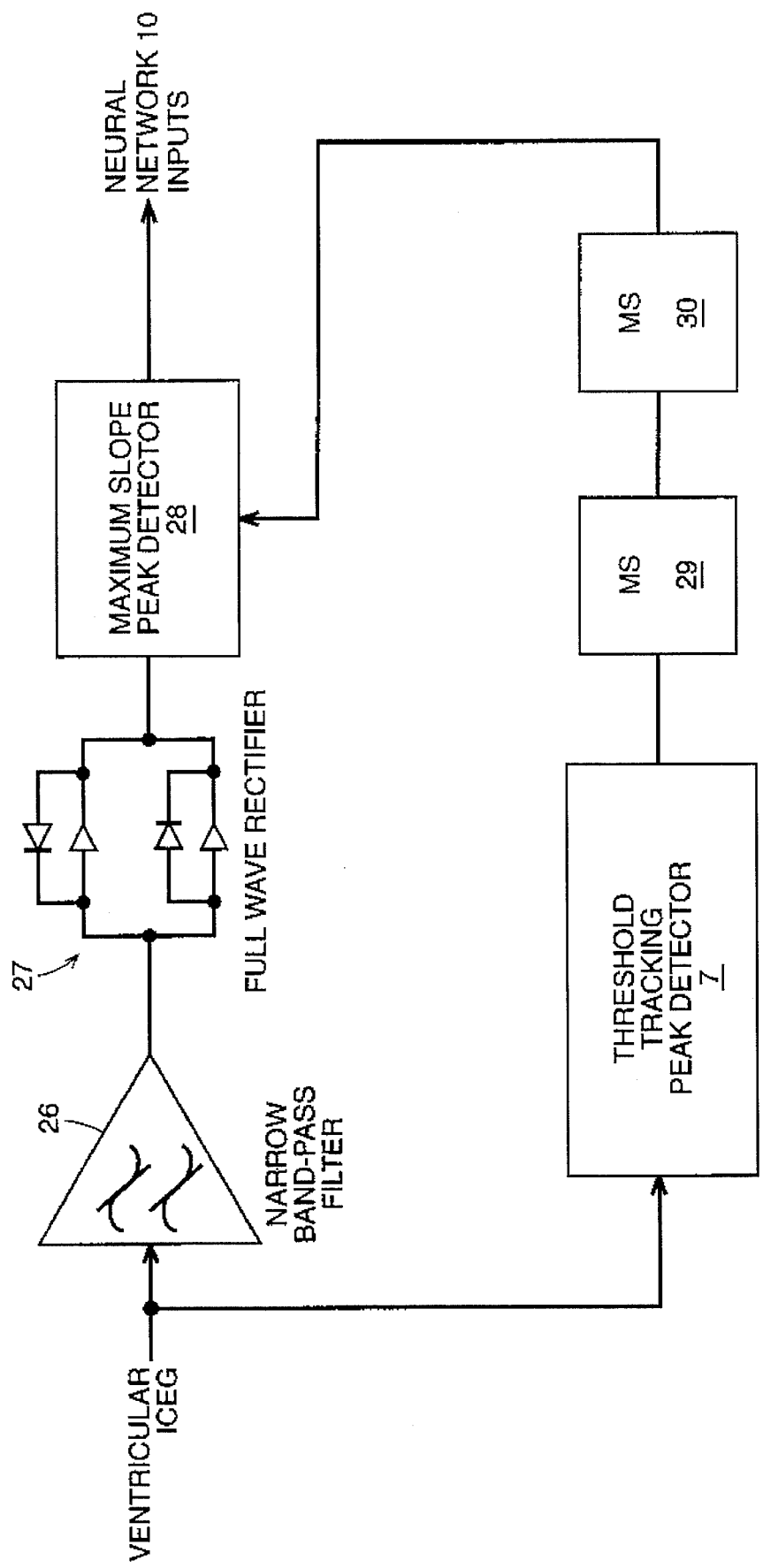
FIG. 7 is a block diagram showing circuitry for measuring the maximum R-wave gradient.

Referring to FIG. 7, the ventricular ICEG passes through a narrow bandpass filter 26 whose center frequency is 40 Hz and whose pass band is approximately 5 Hz. This ensures that the QRS complex, whose frequencies mostly lie in the range 15–35 Hz, is differentiated by the high pass cut-off of the filter 23. The output of the filter passes to a full wave rectifier 27, and a peak detection circuit 28 which may be reset by the threshold tracking and peak detector 7, followed by two monostable multivibrators 29, 30 used as a delay. The peak detector then outputs the maximum slope of the Q-, R- or S- wave gradient. It may be restricted to one sign (positive or negative) by modifying the rectifier circuit. This maximum slope may be input directly to the neural network 10 or further processed by an averaging circuit as described previously.

QR AND RS AREA FEATURE

Figure 8:
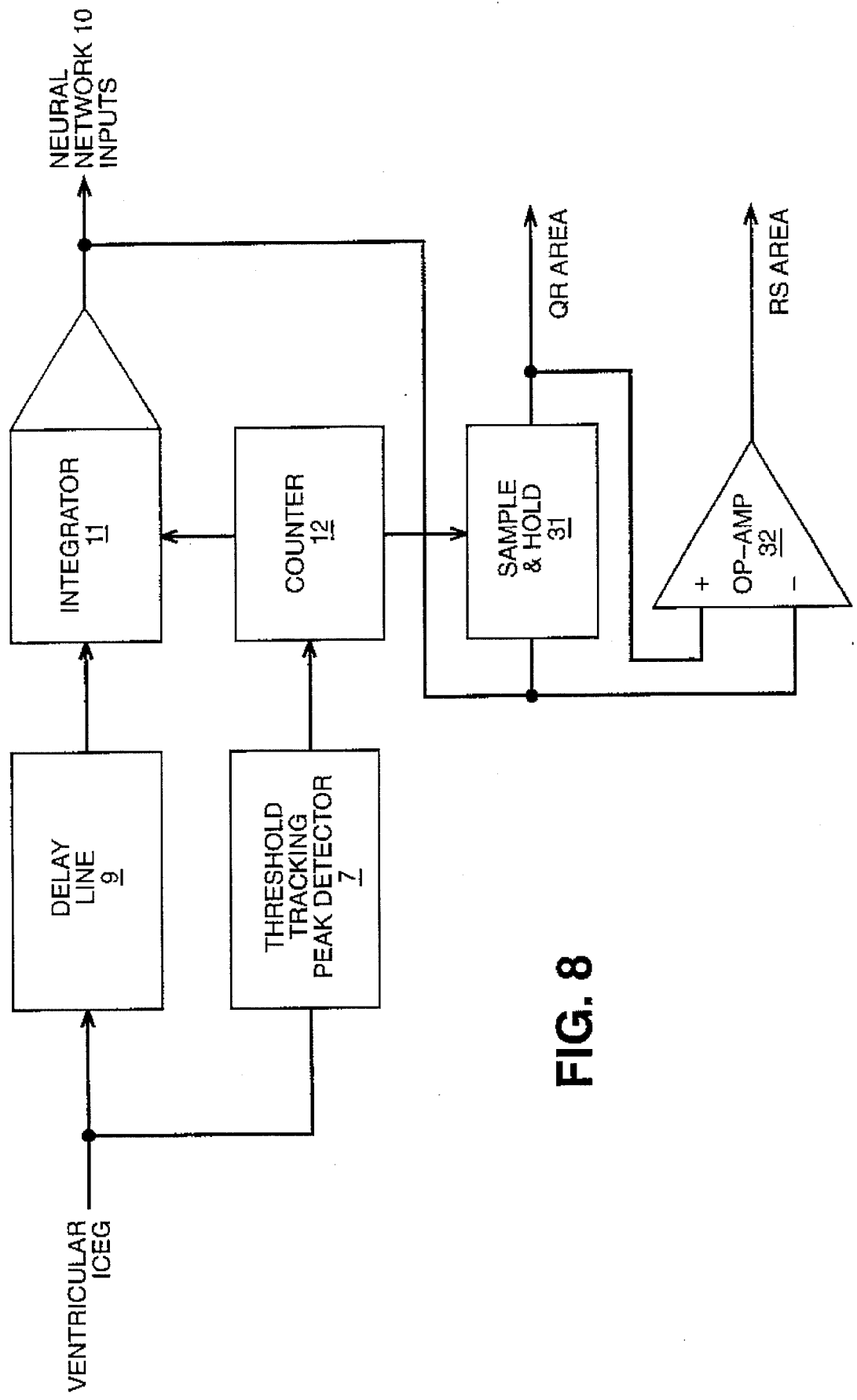
FIG. 8 is a block diagram depicting the circuitry required for extracting the QR and RS area features from the ventricular ICEG.

Referring to FIG. 8, the ventricular ICEG may be integrated, as described previously, but in two time periods demarcated by the threshold tracking peak detection signal. The ICEG is fed into the sample delay line 9. It is tapped and input to the integrator 11. The output of the integrator is stored in a sample and hold circuit 31 on reaching the peak as determined by the threshold tracking peak detector 7 and a counter 12. This is the QR area signal. The integration is continued and the QR area is subtracted from it at the end of the integration period by means of an operational amplifier 32. This gives the RS area. Both these signals are then sent to the inputs of the neural network 10 with or without further processing by averaging, as described previously.

NEURAL NETWORK

The neural network 10 may be of any type, but the preferred embodiment is a multilayer "perceptron" with one hidden layer. The number of neurons in the hidden layer may range from five to 30 and the number of output neurons from 2 to 20. In a typical application, the number of hidden layer neurons is seven and the number of output neurons is five. Each output neuron corresponds to a rhythm classification and produces a value in the range of zero to one which can be likened to the probability of the rhythm belonging to that classification. The network may be implemented as a program on a microprocessor or as an analog network. The preferred embodiment is as an analog network with weights stored on capacitors being periodically refreshed from digital random access memory (RAM) through digital to analog convertors (DAC) and multiplied by the input signals in four quadrant analog multipliers, or, alternatively, having digital weights multiplied by the input signals in a multiplying DAC. The DAC is preferably of the switched capacitor type.

The neural network 10 is trained by the back propagation algorithm using general examples or the patient's own rhythms which may include sinus rhythm, bradycardia, ventricular ectopic beats, atrial ectopic beats, atrial fibrillation, ventricular fibrillation, sinus tachycardia and ventricular tachycardia. The network may be one described in "Working With Neural Networks", by D. Hammerstrom, IEEE Spectrum, July, 1993, pp. 46–53. Further, the neural network may comprise one or more hierarchical levels of the type shown in the aforementioned U.S. patent application Ser. No. 07/918,934 now U.S. Pat. No. 5,251,626 to P. Nickolls et al, which is assigned to the assignee of the present invention and is hereby incorporated by reference.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What is claimed is:

1. A device for monitoring and classifying cardiac rhythms of a patient's heart, comprising:

means for coupling to at least one of an atrium and a ventricle of the heart, for sensing respective ones of an atrial and a ventricular thereof as waveforms which are characteristic of respective cardiac rhythms;

feature extraction means coupled to said coupling means and responsive to the sensed waveforms, for extracting from said waveforms features relating to the timing of events and the morphology of the waveforms;

neural network means coupled to said feature extraction means for classifying said morphological features, said neural network means further including first means for discriminating between features relating to rhythms of normal origin and rhythms of pathological origin, and second means for discriminating between features relating to different kinds of tachycardia of pathological origin said first and second discriminating means generating output signals classifying cardiac rhythms into physiological and pathological categories;

wherein said neural network means includes means for setting a time interval;

wherein said feature extraction means includes a threshold tracking peak detector means to provide at least one fiducial point in each sensed waveform, said fiducial point being one of a maximum positive and minimum negative peak within said time of the threshold being exceeded by the waveform;

wherein said feature extraction means integrates the waveform about its fiducial point for a predetermined period of time before and after said point.

2. A device according to claim 1 wherein:

said classifying means utilizes said first and second means to discriminate between different types of rhythms whose rates may overlap in frequency.

3. A device for monitoring and classifying cardiac rhythms of a patient's heart, comprising:

means for coupling to at least one of an atrium and a ventricle of the heart, for sensing respective ones of an atrial and a ventricular waveforms which are characteristic of respective cardiac rhythms;

feature extraction means coupled to said coupling means and responsive to the sensed waveforms, for extracting from said waveforms features relating to the timing of events and the morphology of the waveforms;

neural network means coupled to said feature extraction means for classifying said morphological features, said neural network means further including first means for discriminating between features relating to rhythms of normal origin and rhythms of pathological origin, and second means for discriminating between features relating to different kinds of tachycardia of pathological origin wherein said neural network means includes means for setting a time interval;

said first and second discriminating means generating output signals classifying cardiac rhythms into physiological and pathological categories;

wherein said feature extraction means includes a threshold tracking peak detector means to provide at least one fiducial point in each sensed waveform, said fiducial point being one of a maximum positive and minimum negative peak within a preselected time of the threshold being exceeded by the waveform;

wherein said feature extraction means takes sums of differences of samples taken at predetermined intervals from the waveform symmetrically about its fiducial point.

4. A device for monitoring and classifying cardiac rhythms of a patient's heart, comprising:

means for coupling to at least one of an atrium and a ventricle of the heart, for sensing respective ones of an atrial and a ventricular waveforms which are characteristic of respective cardiac rhythms;

feature extraction means coupled to said coupling means and responsive to the sensed waveforms, for extracting from said waveforms features relating to the timing of events and the morphology of the waveforms;

neural network means coupled to said feature extraction means for classifying said morphological features, said neural network means further including first means for discriminating between features relating to rhythms of normal origin and rhythms of pathological origin, and second means for discriminating between features relating to different kinds of tachycardia of pathological origin wherein said neural network means includes means for setting a time interval;

said first and second discriminating means generating output signals classifying cardiac rhythms into physiological and pathological categories;

wherein said feature extraction means includes a threshold tracking peak detector means to provide at least one fiducial point in each sensed waveform, said fiducial point being one of a maximum positive and minimum negative peak within a preselected time of the threshold being exceeded by the waveform;

wherein said feature extraction means further includes a plurality of bandpass filters and integrators for filtering the waveform through said filters and integrators during the interval between successive fiducial points.

5. A device for monitoring and classifying cardiac rhythms of a patient's heart, comprising:

means for coupling to at least one of an atrium and a ventricle of the heart, for sensing respective one of an atrial and a ventricular thereof as waveforms which are characteristic of respective cardiac rhythms;

feature extraction means coupled to said coupling means and responsive to the sensed waveforms, for extracting from said waveforms features relating to the timing of events and the morphology of the waveforms;

neural network means coupled to said feature extraction means for classifying said morphological features, said neural network means further including first means for discriminating between features relating to rhythms of normal origin and rhythms of pathological origin, and second means for discriminating between features relating to different kinds of tachycardia of pathological origin;

wherein said neural network means includes means for setting a time interval;

said first and second discriminating means generating output signals classifying cardiac rhythms into physiological and pathological categories;

wherein said feature extraction means includes a threshold tracking peak detector means to provide at least one fiducial point in each sensed waveform, said fiducial point being one of a maximum positive and minimum negative peak within a preselected time of the threshold being exceeded by the waveform;

wherein said feature extraction means further includes means for determining the crossings of a waveform through zero amplitude for determining the crossings of the waveforms through zero amplitude.

6. A device for monitoring and classifying cardiac rhythms of a patient's heart, comprising:

means for coupling to at least one of an atrium and a ventricle of the heart, for sensing respective ones of an atrial and a ventricular thereof as waveforms which are characteristic of respective cardiac rhythms;

feature extraction means coupled to said coupling means and responsive to the sensed waveforms, for extracting from said waveforms features relating to the timing of events and the morphology of the waveforms;

neural network means coupled to said feature extraction means for classifying said morphological features, said neural network means further including first means for discriminating between features relating to rhythms of normal origin and rhythms of pathological origin, and second means for discriminating between features relating to different kinds of tachycardia of pathological origin;

wherein said neural network means includes means for setting a time interval;

said first and second discriminating means generating output signals classifying cardiac rhythms into physiological and pathological categories;

wherein said feature extraction means includes a threshold tracking peak detector means to provide at least one fiducial point in each sensed waveform, said fiducial point being one of a maximum positive and minimum negative peak within a preselected time of the threshold being exceeded by the waveform;

wherein said feature extraction means determines an interval between successive atrial and ventricular complexes of the waveform; and wherein said classifying means classifies as of pathological origin those of such tachycardias in which atrioventricular intervals change rapidly in sequence.

* * * * *